US008647847B2

(12) United States Patent
Nonaka

(10) Patent No.: US 8,647,847 B2
(45) Date of Patent: Feb. 11, 2014

(54) L-CYSTEINE-PRODUCING BACTERIUM AND A METHOD FOR PRODUCING L-CYSTEINE

(75) Inventor: Gen Nonaka, Kawasaki (JP)

(73) Assignee: Ajinomoto Co., Inc., Tokyo (JP)

(*) Notice: Subject to any disclaimer, the term of this patent is extended or adjusted under 35 U.S.C. 154(b) by 0 days.

(21) Appl. No.: 13/482,142

(22) Filed: May 29, 2012

(65) Prior Publication Data

US 2012/0288902 A1 Nov. 15, 2012

Related U.S. Application Data

(63) Continuation of application No. PCT/JP2010/071102, filed on Nov. 26, 2010.

(30) Foreign Application Priority Data

Nov. 30, 2009 (JP) ................................. 2009-272358

(51) Int. Cl.
C12P 13/12 (2006.01)

(52) U.S. Cl.
USPC .......................................... 435/113; 435/243

(58) Field of Classification Search
USPC .............................. 435/113, 252.3
See application file for complete search history.

(56) References Cited

U.S. PATENT DOCUMENTS

| | | | |
|---|---|---|---|
| 5,618,716 | A | 4/1997 | Burlingame |
| 5,972,663 | A | 10/1999 | Winterhalter et al. |
| 6,218,168 | B1 | 4/2001 | Leinfelder et al. |
| 8,008,048 | B2 | 8/2011 | Nonaka et al. |
| 2003/0077766 | A1 | 4/2003 | Takagi et al. |
| 2003/0186393 | A1 | 10/2003 | Takagi et al. |
| 2004/0029129 | A1 | 2/2004 | Wang et al. |
| 2005/0009162 | A1 | 1/2005 | Maier et al. |
| 2005/0112731 | A1 | 5/2005 | Kashiwagi et al. |
| 2005/0221453 | A1 | 10/2005 | Takagi et al. |
| 2008/0076163 | A1 | 3/2008 | Takagi et al. |
| 2009/0226982 | A1 | 9/2009 | Takagi et al. |
| 2009/0226984 | A1 | 9/2009 | Nonaka et al. |
| 2010/0093045 | A1 | 4/2010 | Takagi et al. |
| 2010/0209977 | A1 | 8/2010 | Takumi et al. |
| 2010/0216196 | A1 | 8/2010 | Nonaka et al. |
| 2010/0233765 | A1 | 9/2010 | Nonaka et al. |
| 2011/0033902 | A1 | 2/2011 | Nonaka et al. |
| 2011/0177566 | A1 | 7/2011 | Savrasova et al. |
| 2011/0212496 | A1 | 9/2011 | Takikawa et al. |

FOREIGN PATENT DOCUMENTS

| | | |
|---|---|---|
| JP | 6-510911 | 12/1994 |
| JP | 11-155571 | 6/1999 |
| JP | 2002-233384 | 8/2002 |
| JP | 2003-169668 | 6/2003 |
| JP | 2005-245311 | 9/2005 |
| JP | 2005-287333 | 10/2005 |
| WO | WO01/27307 | 4/2001 |
| WO | WO02/077183 | 10/2002 |
| WO | WO2011/065469 | 6/2011 |

OTHER PUBLICATIONS

Sousa et al., The ARO4 gene of *Candida albicans* encodes a tyrosine-sensitive DAHP synthase: evolution, functional conservation and phenotype of Aro4p-, Aro4p-deficient mutants. Microbiology 148:1291-1303, 2002.*
Chica et al., Semi-rational approaches to engineering enzyme activity: combining the benefits of directed evolution and rational design. Current Opin. Biotechnol. 16 (4):378-84, 2005.*
Sen et al., Developments in Directed Evolution for Improving Enzyme Functions. Appl Biochem Biotechnol. 143 (3):212-23, 2007.*
BioCyc Home Page, *Escherichia coli* K-12 Substr. MG1655 Gene yciW (Oct. 14, 2009), (biocyc.org/ECOLI/NEW-IMAGE?type=Gene&object=G6640; retrieved Jul. 19, 2012).
International Preliminary Report on Patentability for PCT Patent App. No. PCT/JP2010/071102 (Jul. 10, 2012).
Dassler, T., et al., "Identification of a major facilitator protein from *Escherichia coli* involved in efflux of metabolites of the cysteine pathway," Mol. Microbiol. 2000;36(5):1101-1112.
Gyaneshwar, P., et al., "Sulfur and Nitrogen Limitation in *Escherichia coli* K-12: Specific Homeostatic Responses," J. Bacteriol. 2005;187(3):1074-1090.
Miller, E. N., et al., "Furfural Inhibits Growth by Limiting Sulfur Assimilation in Ethanologenic *Escherichia coli* Strain LY180," Applied Environmen. Microbiol. 2009;75(19):6132-6141.
Wang, S., et al., "Transcriptomic Response of *Escherichia coli* O157:H7 to Oxidative Stress," Applied Environmen. Microbiol. 2009;75(19):6110-6123.
International Search Report for PCT Patent App. No. PCT/JP2010/071102 (Feb. 22, 2011).
Baba, T., et al., "Construction of *Escherichia coil* K-12 in-frame, single-gene knockout mutants: the Keio collection," Mol. Sys. Biol. 2006:1-8.
Kitagawa. M., et al., "Complete set of ORF clones of *Escherichia coli* ASKA library (A Complete Set of *E. coli* K-12 ORF Archive): Unique Resources for Biological Research," DNA Res. 2005:12:291-299.
Supplementary European Search Report for EP Patent App. No. 10833315.4 (Oct. 2, 2013).

* cited by examiner

*Primary Examiner* — Tekchand Saidha
*Assistant Examiner* — Rama P Ramanujam
(74) *Attorney, Agent, or Firm* — Shelly Guest Cermak; Cermak Nakajima LLP

(57) ABSTRACT

An L-cysteine-producing bacterium is provided, as well as a method for producing L-cysteine etc. using the bacterium by developing a novel technique for improving L-cysteine-producing ability of a bacterium. By culturing a bacterium belonging to the family Enterobacteriaceae, which has L-cysteine-producing ability and is modified so that activity of a protein encoded by the yciW gene, for example, a protein defined by the following (A) or (B), is reduced, in a medium, and collecting L-cysteine, L-cystine, a derivative thereof, or a mixture thereof from the medium, these compounds are produced: (A) a protein having the amino acid sequence shown in SEQ ID NO: 2, (B) a protein having the amino acid sequence shown in SEQ ID NO: 2, but which includes substitution, deletion, insertion, or addition of one or several amino acid residues, reduction of which activity in the bacterium results in improvement in the L-cysteine-producing ability.

8 Claims, No Drawings

L-CYSTEINE-PRODUCING BACTERIUM AND A METHOD FOR PRODUCING L-CYSTEINE

This application is a Continuation of, and claims priority under 35 U.S.C. §120 to, International Application No. PCT/JP2010/071102, filed Nov. 26, 2010, and claims priority therethrough under 35 U.S.C. §119 to Japanese Patent Application No. 2009-272358, filed Nov. 30, 2009, the entireties of which are incorporated by reference herein. Also, the Sequence Listing filed electronically herewith is hereby incorporated by reference (File name: 2012-05-29T_US-480_Seq_List; File size: 102 KB; Date recorded: May 29, 2012).

BACKGROUND OF THE INVENTION

1. Field of the Invention

The present invention relates to a method for producing L-cysteine or a related substance thereof. More precisely, the present invention relates to a bacterium suitable for production of L-cysteine or a related substance thereof, and a method for producing L-cysteine or a related substance thereof utilizing the bacterium. L-cysteine and related substances thereof are useful in the fields of drugs, cosmetics, and foods.

2. Brief Description of the Related Art

L-cysteine is conventionally obtained by extraction from keratin-containing substances such as hair, horns, and feathers, or by converting the precursor DL-2-aminothiazoline-4-carboxylic acid using a microbial enzyme. L-cysteine has been produced on a large scale by an immobilized enzyme method utilizing a novel enzyme. Furthermore, it has also been attempted to produce L-cysteine by fermentation utilizing a microorganism.

As microorganisms having the ability to produce L-cysteine, a coryneform bacterium is known, for example, in which intracellular serine acetyltransferase activity is increased (Japanese Patent Laid-open (Kokai) No. 2002-233384). A technique has been reported of increasing L-cysteine-producing ability by incorporating a mutant serine acetyltransferase of which feedback inhibition by L-cysteine is attenuated (Japanese Patent Laid-open (Kokai) No. 11-155571, U.S. Patent Published Application No. 20050112731, and U.S. Pat. No. 6,218,168).

Furthermore, as microorganisms in which L-cysteine-producing ability is enhanced by suppressing the system which acts to decompose L-cysteine, there are known coryneform bacteria or *Escherichia* bacteria in which the activity of cystathionine-β-lyase (Japanese Patent Laid-open (Kokai) No. 11-155571), tryptophanase (Japanese Patent Laid-open (Kokai) No. 2003-169668), or O-acetylserine sulfhydrylase B (Japanese Patent Laid-open (Kokai) No. 2005-245311) is attenuated or deleted.

Moreover, it is known that the ydeD gene coding for the YdeD protein participates in secretion of metabolic products of the L-cysteine pathway (Dassler et al., Mol. Microbiol., 36, 1101-1112 (2000)). Furthermore, techniques have been reported of enhancing L-cysteine-producing ability by increasing expression of the mar locus, emr locus, acr locus, cmr locus, mex gene, bmr gene or qacA gene (U.S. Pat. No. 5,972,663), or emrAB, emrKY, yojIH, acrEF, bcr or cusA gene (Japanese Patent Laid-open (Kokai) No. 2005-287333). These loci/genes code for proteins which are able to secrete a cytotoxic substance from the cells.

Furthermore, an *Escherichia coli* is known to produce L-cysteine, in which the activity of the positive transcriptional control factor of the cysteine regulon encoded by the cysB gene is increased (International Patent Publication WO01/27307).

Furthermore, a mutant serA coding for 3-phosphoglycerate dehydrogenase is known, of which feedback inhibition by serine is attenuated, and use thereof for L-cysteine production by *Escherichia coli* has been suggested (U.S. Pat. No. 5,856,148 and U.S. Patent Published Application No. 20050009162).

Although yciW is registered in the database EcoCyc as a gene coding for a predicted oxidoreductase (BioCyc Home Page, *Escherichia coli* K-12-substr. MG1655 Gene: yciW [searched on Oct. 14, 2009], Internet URL >biocyc (dot) org/ECOLI/NEW-IMAGE?type=GENE&object=G6640>), the actual functions thereof are unknown, and the relation thereof with L-cysteine production is not known.

Moreover, although it has been reported that the yciW gene is up-regulated by depletion of a sulfur source (Gyaneshwar, P. et al., J. Bacteriol., 187:1074-1090 (2005)), furfural (Elliot N., Miller, E. N., et al., Appl. Envir. Microbiol., 10.1128-/AEM.01187-09 (2009)), and oxidative stress (Wang, S., et al., Appl. Envir. Microbiol., 10.1128/AEM.00914-09 (2009)), it is mentioned in all the documents only as one of a large number of genes that showed variation of expression in microarray experiments, and relation thereof with L-cysteine production has not been suggested.

SUMMARY OF THE INVENTION

An aspect of the present invention is to provide an L-cysteine-producing bacterium, and a method for producing L-cysteine, L-cystine, a derivative thereof, or a mixture thereof by developing a novel technique for improving L-cysteine-producing ability of a bacterium.

It has been found that L-cysteine-producing ability of a bacterium can be improved by modifying the bacterium so that the activity of a protein encoded by the yciW gene is reduced.

It is an aspect of the present invention to provide a bacterium belonging to the family Enterobacteriaceae, which is able to produce L-cysteine, and is modified to have reduced activity of a protein encoded by the yciW gene, as compared to a non-modified bacterium.

It is a further aspect of the present invention to provide the bacterium as described above, wherein the activity of the protein is reduced by reducing expression of the yciW gene, or by disrupting the yciW gene.

The bacterium as mentioned above, wherein the protein is selected from the group consisting of:

(A) a protein comprising the amino acid sequence shown in SEQ ID NO: 2, (B) a protein comprising the amino acid sequence shown in SEQ ID NO: 2, but which includes one or more substitutions, deletions, insertions, or additions of one or several amino acid residues, wherein said reduced activity results in an improved ability to produce L-cysteine.

It is a further aspect of the present invention to provide the bacterium as described above, wherein the yciW gene is a DNA selected from the group consisting of:

(a) a DNA comprising the nucleotide sequence of the positions 301 to 1428 in the nucleotide sequence of SEQ ID NO: 1, (b) a DNA hybridizable with a complementary sequence of the nucleotide sequence of the positions 301 to 1428 in the nucleotide sequence of SEQ ID NO: 1, or a probe that can be prepared from the nucleotide sequence, under stringent conditions, and which encodes a protein, wherein said reduced activity results in an improved ability to produce L-cysteine.

It is a further aspect of the present invention to provide the bacterium as described above, which is modified to further comprise at least one of the following characteristics:
  i) serine acetyltransferase activity is increased,
  ii) expression of the ydeD gene is increased, and
  iii) 3-phosphoglycerate dehydrogenase activity is increased.

It is a further aspect of the present invention to provide the bacterium as described above, which is an *Escherichia* bacterium.

It is a further aspect of the present invention to provide the bacterium as described above, which is *Escherichia coli*.

It is a further aspect of the present invention to provide a method for producing L-cysteine, L-cystine, a derivative thereof, or a mixture thereof, which comprises culturing the bacterium as described above in a medium and collecting L-cysteine, L-cystine, a derivative thereof, or a mixture thereof from the medium.

It is a further aspect of the present invention to provide the method as described above, wherein the derivative of L-cysteine is a thiazolidine derivative.

According to the present invention, L-cysteine-producing ability of a bacterium can be improved. Furthermore, according to the present invention, L-cysteine, L-cystine, a derivative thereof, or a mixture thereof can be efficiently produced.

DESCRIPTION OF THE PREFERRED EMBODIMENTS

<1> Bacterium

The bacterium can belong to the family Enterobacteriaceae, which has L-cysteine-producing ability and is modified so that activity of the protein encoded by the yciW gene is reduced. The L-cysteine-producing ability can mean that the bacterium can produce L-cysteine in a medium or the cells of the bacterium and accumulate it in such an amount that L-cysteine can be collected from the medium or the cells, when the bacterium is cultured in the medium. A bacterium having L-cysteine-producing ability can mean that the bacterium can produce and accumulate L-cysteine in a medium in a larger amount as compared with a wild-type strain or a parent strain, or that the bacterium can produce and accumulate L-cysteine in a medium in an amount of 0.05 g/L or more, 0.1 g/L or more, or 0.2 g/L or more.

A portion of L-cysteine produced by the bacterium can be converted into L-cystine in the medium by the formation of a disulfide bond. Furthermore, S-sulfocysteine can be generated by the reaction of L-cysteine and thiosulfate contained in the medium (Szczepkowski T. W., Nature, vol. 182 (1958)) as described later. Furthermore, L-cysteine generated in bacterial cells can be condensed with a ketone or aldehyde, for example, pyruvic acid, which is present in the cells, to produce a thiazolidine derivative via a hemithioketal as an intermediate (refer to Japanese Patent No. 2992010). These thiazolidine derivative and hemithioketal can exist as an equilibrated mixture. Therefore, the L-cysteine-producing ability is not limited to an ability to accumulate only L-cysteine in a medium or cells, but also includes an ability to accumulate, in addition to L-cysteine, L-cystine, a derivative thereof such as S-sulfocysteine, a thiazolidine derivative, or a hemithioketal, or a mixture thereof in the medium. Furthermore, L-cysteine can be used as a starting material in the biosyntheses of γ-glutamylcysteine, glutathione, cystathionine, homocysteine, methionine, S-adenosylmethionine, and so forth. Therefore, by using a bacterium having an ability to produce any of these compounds in addition to the ability to produce L-cysteine, these compounds can be produced. Therefore, the L-cysteine-producing ability can also include an ability to accumulate another compound to be produced via L-cysteine.

The bacterium having L-cysteine-producing ability can inherently have L-cysteine-producing ability, or it can be obtained by modifying a bacterium such as those described below by mutagenesis or a recombinant DNA technique so that it acquires L-cysteine-producing ability. In the present invention, unless specifically mentioned, the term L-cysteine can be used to refer to reduced type L-cysteine, L-cystine, such a derivative as those mentioned above, or a mixture thereof.

The bacterium is not particularly limited so long as the bacterium belongs to the family Enterobacteriaceae such as those of the genera *Escherichia, Enterobacter, Pantoea, Klebsiella, Serratia, Erwinia, Salmonella*, and *Morganella*, and has the ability to produce an L-amino acid. Specifically, those classified into the family Enterobacteriaceae according to the taxonomy used in the NCBI (National Center for Biotechnology Information) database (ncbi (dot) nlm (dot) nih (dot) gov/Taxonomy/Browser/wwwtax.cgi?id=91347) can be used. As a parent strain belonging to the family Enterobacteriaceae used for the modification, it is desirable to use, especially, a bacterium of the genus *Escherichia, Enterobacter, Pantoea, Erwinia, Enterobacter*, or *Klebsiella*.

Although the *Escherichia* bacteria are not particularly limited, specifically, those described in the work of Neidhardt et al. (Backmann B. J., 1996, Derivations and Genotypes of some mutant derivatives of *Escherichia coli* K-12, p. 2460-2488, Table 1, In F. D. Neidhardt (ed.), *Escherichia coli* and *Salmonella* Cellular and Molecular Biology/Second Edition, American Society for Microbiology Press, Washington, D.C.) can be used. Among them, for example, *Escherichia coli* can be used. Specific examples of *Escherichia coli* include *Escherichia coli* W3110 (ATCC 27325), *Escherichia coli* MG1655 (ATCC 47076), and so forth, which are derived from the prototype wild-type strain, the K12 strain.

These strains are available from, for example, the American Type Culture Collection (Address: P.O. Box 1549, Manassas, Va. 20108, United States of America). That is, registration numbers are given to each of the strains, and the strains can be ordered by using these registration numbers (refer to atcc (dot) org/). The registration numbers of the strains are listed in the catalogue of the American Type Culture Collection.

Examples of the *Enterobacter* bacteria can include *Enterobacter agglomerans, Enterobacter aerogenes*, and so forth, and examples of the *Pantoea* bacteria can include *Pantoea ananatis*. Some of *Enterobacter agglomerans* were recently reclassified into *Pantoea agglomerans, Pantoea ananatis*, or *Pantoea stewartii* on the basis of nucleotide sequence analysis of 16S rRNA etc. A bacterium belonging to the genus *Enterobacter* or *Pantoea* can be used so long as the bacterium is classified into the family Enterobacteriaceae.

In particular, *Pantoea* bacteria, *Erwinia* bacteria, and *Enterobacter* bacteria are classified as γ-proteobacteria, and they are taxonomically very close to one another (J. Gen. Appl. Microbiol., December 1997, 43(6), 355-361; International Journal of Systematic Bacteriology, October 1997, 1061-1067). In recent years, some bacteria belonging to the genus *Enterobacter* were reclassified into *Pantoea agglomerans, Pantoea dispersa*, or the like, on the basis of DNA-DNA hybridization experiments etc. (International Journal of Systematic Bacteriology, July 1989, 39(3), 337-345). Furthermore, some bacteria belonging to the genus *Erwinia* were reclassified into *Pantoea ananas* or *Pantoea stewartii* (refer to International Journal of Systematic Bacteriology, January 1993, 43(1), 162-173).

Examples of the *Enterobacter* bacteria include *Enterobacter agglomerans*, *Enterobacter aerogenes*, and so forth. Specifically, the strains exemplified in European Patent Laid-open No. 952221 can be used.

A typical strain of the genus *Enterobacter* includes the *Enterobacter agglomerans* ATCC 12287 strain.

Typical strains of the *Pantoea* bacteria can include *Pantoea ananatis*, *Pantoea stewartii*, *Pantoea agglomerans*, and *Pantoea citrea*.

Specific examples of *Pantoea ananatis* can include the *Pantoea ananatis* AJ13355 strain and SC17 strain. The SC17 strain was selected as a low phlegm-producing mutant strain from the AJ13355 strain (FERM BP-6614) isolated from soil in Iwata-shi, Shizuoka-ken, Japan. This strain can proliferate in a low pH medium containing L-glutamic acid and a carbon source (U.S. Pat. No. 6,596,517).

The *Pantoea ananatis* AJ13355 strain was deposited at the National Institute of Bioscience and Human-Technology, Agency of Industrial Science and Technology, Ministry of International Trade and Industry (currently, the National Institute of Advanced Industrial Science and Technology, International Patent Organism Depositary, Address: Tsukuba Central 6, 1-1, Higashi 1-Chome, Tsukuba-shi, Ibaraki-ken, 305-8566, Japan) on Feb. 19, 1998 and assigned an accession number of FERM P-16644. The strain was then converted to an international deposit under the provisions of Budapest Treaty on Jan. 11, 1999 and assigned an accession number of FERM BP-6614. This strain was identified as *Enterobacter agglomerans* when it was isolated and deposited as the *Enterobacter agglomerans* AJ13355 strain. However, the strain was recently reclassified into *Pantoea ananatis* on the basis of nucleotide sequence analysis of 16S rRNA and so forth.

The *Pantoea ananatis* SC17 strain was deposited on Feb. 4, 2009 at the National Institute of Advanced Industrial Science and Technology, International Patent Organism Depository (Address: Tsukuba Central 6, 1-1, Higashi 1-Chome, Tsukuba-shi, Ibaraki-ken, 305-8566, Japan), and assigned an accession number of FERM BP-11091.

Examples of the *Erwinia* bacteria can include *Erwinia amylovora* and *Erwinia carotovora*, and examples of the *Klebsiella* bacteria can include *Klebsiella planticola*.

Hereinafter, methods for imparting L-cysteine-producing ability to bacteria belonging to the family Enterobacteriaceae, or methods for enhancing L-cysteine-producing ability of such bacteria are described.

To impart L-cysteine-producing ability to a bacterium, methods conventionally employed in the breeding of coryneform bacteria, *Escherichia* bacteria, and so forth can be used. Such methods include acquiring an auxotrophic mutant strain, an analogue resistant strain, or a metabolic regulation mutant strain, or constructing a recombinant strain in which an L-cysteine biosynthesis enzyme is overexpressed, and so forth (see "Amino Acid Fermentation", Gakkai Shuppan Center (Ltd.), 1st Edition, published May 30, 1986, pp. 77-100). In the breeding of L-cysteine-producing bacteria, the above-described property(s) such as auxotrophy, analogue resistance, and metabolic regulation mutation can be imparted alone or in combinations of two or more. Expression of L-cysteine biosynthesis enzyme(s) can be enhanced alone or in combinations of two or more. Furthermore, imparting such properties as auxotrophy, analogue resistance, and metabolic regulation mutation can be combined with enhancing a biosynthesis enzyme.

An auxotrophic mutant strain, L-cysteine analogue resistant strain, or metabolic regulation mutant strain having L-cysteine-producing ability can be obtained by subjecting a parent strain or wild-type strain to conventional mutagenesis, such as exposure to X-rays or UV irradiation or a treatment with a mutagen such as N-methyl-N'-nitro-N-nitrosoguanidine (NTG) or ethyl methanesulfonate (EMS), and then selecting a strain exhibiting autotrophy, analogue resistance, or a metabolic regulation mutation and having L-amino acid-producing ability from the obtained mutant strains.

L-cysteine-producing ability of a bacterium can be improved by enhancing the activity of an enzyme of the L-cysteine biosynthesis pathway or an enzyme involved in generation of a compound which acts as a substrate in the pathway such as L-serine, for example, 3-phosphoglycerate dehydrogenase and serine acetyltransferase. Because 3-phosphoglycerate dehydrogenase is inhibited by feedback inhibition by serine, the enzymatic activity of this enzyme can be enhanced by incorporating a mutant type serA gene coding for a mutant 3-phosphoglycerate dehydrogenase of which feedback inhibition is attenuated or eliminated into a bacterium.

Furthermore, serine acetyltransferase is inhibited by feedback inhibition by L-cysteine. Hence, the enzymatic activity of this enzyme can be enhanced by incorporating a mutant type cysE gene coding for a serine acetyltransferase of which feedback inhibition is attenuated or eliminated into a bacterium.

L-cysteine-producing ability can also be enhanced by enhancing expression of the ydeD gene coding for the YdeD protein (Dabler et al., Mol. Microbiol., 36, 1101-1112 (2000)) or the yfiK gene coding for the YfiK protein (Japanese Patent Laid-open (Kokai) No. 2004-49237).

The bacterium can also be modified to have at least one of the following characteristics:
  i) serine acetyltransferase activity is increased,
  ii) expression of the ydeD gene is increased, and
  iii) 3-phosphoglycerate dehydrogenase activity is increased.

Furthermore, the L-cysteine-producing ability can also be improved by enhancing the activity of the sulfate/thiosulfate transport system. The sulfate/thiosulfate transport system proteins are encoded by the cysPTWAM gene cluster (Japanese Patent Laid-open (Kokai) No. 2005-137369, European Patent No. 1528108).

The L-cysteine-producing ability of a bacterium can also be improved by increasing expression of the yeaS gene (European Patent Laid-open No. 1016710).

Specific examples of L-cysteine-producing bacteria can include, but are not limited to, strains belonging to the genus *Escherichia* such as the *E. coli* JM15 strain transformed with multiple kinds of cysE alleles encoding serine acetyltransferase (SAT) resistant to feedback inhibition (U.S. Pat. No. 6,218,168), *E. coli* W3110 strain having an overexpressed gene encoding a protein suitable for secretion of a cytotoxic substance (U.S. Pat. No. 5,972,663), *E. coli* strain in which cysteine desulfhydrase activity is decreased (Japanese Patent Laid-open (Kokai) No. 11-155571), and *E. coli* W3110 strain in which the activity of the positive transcriptional control factor of the cysteine regulon encoded by the cysB gene is increased (WO01/27307), *E. coli* having the plasmid pACYC-DES (Japanese Patent Laid-open (Kokai) No. 2005-137369 (U.S. Patent Published Application No. 20050124049(A1), European Patent Laid-open No. 1528108 (A1))) containing the ydeD gene, a mutant cysE gene, and a mutant serA5 gene, and so forth. pACYC-DES is a plasmid obtained by inserting the above three kinds of genes into pACYC184, and expression of each of the genes is controlled by the PompA promoter.

Proteins having the cysteine desulfhydrase activity of *E. coli* can include cystathionine-β-lyase (metC product, Japanese Patent Laid-open No. 11-155571, Chandra et al., Biochemistry, 21 (1982) 3064-3069), tryptophanase (tnaA product, Japanese Patent Laid-open (Kokai) No. 2003-169668, Austin Newton et al., J. Biol. Chem., 240 (1965) 1211-1218)), O-acetylserine sulfhydrylase B (cysM gene product, Japanese Patent Laid-open (Kokai) No. 2005-245311), and the malY gene product (Japanese Patent Laid-open (Kokai) No. 2005-245311). By decreasing the activities of these proteins, L-cysteine-producing ability can be improved.

The L-cysteine-producing bacterium can have a mutant SAT which is resistant to feedback inhibition. Mutant SATs which are derived from *Escherichia coli* and are resistant to feedback inhibition can include the mutant SAT in which the methionine residue at position 256 is replaced with glutamate residue (Japanese Patent Laid-open No. 11-155571), the mutant SAT in which the methionine residue at position 256 is replaced with isoleucine residue (Denk, D. and Boeck, A., J. General Microbiol., 133, 515-525 (1987)), the mutant SAT having a mutation in the region from the amino acid residue at position 97 to the amino acid residue at position 273 or deletion of the C-terminus region from the amino acid residue at position 227 (International Patent Publication WO97/15673, U.S. Pat. No. 6,218,168), the mutant SAT in which the amino acid sequence corresponding to positions 89 to 96 of wild-type SAT contains one or more mutations, and which is desensitized to the feedback inhibition by L-cysteine (U.S. Patent Published Application No. 20050112731(A1)), the mutant SAT in which the Val residue and the Asp residue at positions 95 and 96 SAT are replaced with Arg residue and Pro residue, respectively (name of the mutant gene: cysE5, WO2005/007841), the mutation by which the threonine residue at position 167 is replaced with an alanine residue (U.S. Pat. No. 6,218,168, U.S. Patent Published Application No. 20050112731(A1)), and so forth.

The SAT gene is not limited to the gene of *Escherichia coli*, and any gene coding for a protein having the SAT activity can be used. An SAT isozyme of *Arabidopsis thaliana* desensitized to the feedback inhibition by L-cysteine is known, and the gene encoding this isozyme can also be used (FEMS Microbiol. Lett., 179, 453-459 (1999)).

If a gene encoding a mutant SAT is introduced into a bacterium, L-cysteine-producing ability is imparted.

For introducing a gene into a bacterium, various vectors which are typically used for protein expression can be used. Examples of such vectors include pUC19, pUC18, pHSG299, pHSG399, pHSG398, RSF1010, pBR322, pACYC184, pMW219, and so forth.

In order to introduce a recombinant vector into a bacterium, methods usually used for transformation of bacteria such as the method of D. A. Morrison (Methods in Enzymology, 68, 326 (1979)), a method of treating recipient cells with calcium chloride to increase permeability of the cells for DNA (Mandel, M. and Higa, A., J. Mol. Biol., 53, 159 (1970)), and a method based on electroporation can be used.

Furthermore, the activity of a protein such as SAT can also be increased by increasing the copy number of the gene coding for the protein. The copy number of a gene can be increased by introducing the gene into a bacterium by using a vector such as those described above, or by introducing multiple copies of the gene into the chromosomal DNA of a bacterium. Multiple copies of the gene are introduced by homologous recombination using a sequence present on the chromosomal DNA in a multiple copy number as a target. A repetitive DNA or inverted repeat present at the ends of a transposon can be used as the sequence present on a chromosomal DNA in a multiple copy number. Alternatively, as disclosed in Japanese Patent Laid-open (Kokai) No. 2-109985, multiple copies of a gene can be introduced into a chromosomal DNA by incorporating them into a transposon and transferring it.

The ability to produce compounds biosynthesized from L-cysteine as a starting material, such as γ-glutamylcysteine, glutathione, cystathionine, homocysteine, methionine, and S-adenosylmethionine, can also be imparted or enhanced by enhancing the activity of an enzyme of the biosynthesis pathway of an objective compound, or by reducing the activity of an enzyme of a pathway branching away from the biosynthesis pathway of an objective compound or an enzyme that decomposes an objective compound.

For example, the ability to produce γ-glutamylcysteine can be enhanced by enhancing the γ-glutamylcysteine synthetase activity, and/or by reducing the glutathione synthetase activity. Furthermore, the ability to produce glutathione can be imparted or enhanced by enhancing the γ-glutamylcysteine synthetase activity and/or the glutathione synthetase activity. Furthermore, by using a mutant γ-glutamylcysteine synthetase resistant to feedback inhibition by glutathione, the ability to produce γ-glutamylcysteine or glutathione can be enhanced. Production of glutathione is described in detail in the review of Li et al. (Yin Li, Gongyuan Wei, Jian Chen, Appl. Microbiol. Biotechnol., 66:233-242 (2004)).

The ability to produce L-methionine can be imparted or enhanced by imparting L-threonine auxotrophy or norleucine resistance (Japanese Patent Laid-open (Kokai) No. 2000-139471). In *E. coli*, the genes of the enzymes involved in the biosynthesis of L-threonine exist as the threonine operon (thrABC), and an L-threonine auxotrophic strain that has lost the biosynthesis ability for L-homoserine and the following compounds can be obtained by, for example, deleting the thrBC moiety. In a norleucine resistant strain, the S-adenosylmethionine synthetase activity is attenuated, and the ability to produce L-methionine is imparted or enhanced. In *E. coli*, S-adenosylmethionine synthetase is encoded by the metK gene. The ability to produce L-methionine can also be imparted or enhanced by deleting the methionine repressor or by enhancing the activity of an enzyme involved in the L-methionine biosynthesis, such as homoserine transsuccinylase, cystathionine γ-synthase and aspartokinase-homoserine dehydrogenase II (Japanese Patent Laid-open (Kokai) No. 2000-139471). In *E. coli*, the methionine repressor is encoded by the metJ gene, homoserine transsuccinylase is encoded by the metA gene, cystathionine γ-synthase is encoded by the metB gene, and aspartokinase-homoserine dehydrogenase II is encoded by the metL gene. Furthermore, by using a mutant homoserine transsuccinylase resistant to feedback inhibition by L-methionine, the ability to produce L-methionine can also be imparted or enhanced (Japanese Patent Laid-open (Kokai) No. 2000-139471, U.S. Patent Published Application No. 20090029424). Because L-methionine is biosynthesized via L-cysteine as an intermediate, the ability to produce L-methionine can also be improved by improving the ability to produce L-cysteine (Japanese Patent Laid-open (Kokai) No. 2000-139471, U.S. Patent Published Application No. 20080311632). Therefore, for imparting or enhancing the ability to produce L-methionine, it is also effective to impart or enhance the ability to produce L-cysteine.

Specific examples of L-methionine-producing bacteria and parent strains used for construction of them include such *E. coli* strains as AJ11539 (NRRL B-12399), AJ11540 (NRRL B-12400), AJ11541 (NRRL B-12401), AJ11542 (NRRL B-12402) (British Patent No. 2075055), 218 strain resistant to norleucine, which is an analogue of L-methionine (VKPM B-8125, Russian Patent No. 2209248), and 73 strain (VKPM B-8126, Russian Patent No. 2215782).

Furthermore, as an L-methionine-producing bacterium or a parent strain which can be used to derive it, AJ13425 derived from the *E. coli* W3110 (FERM P-16808, Japanese Patent Laid-open (Kokai) No. 2000-139471) can also be used. AJ13425 is an L-threonine auxotrophic strain in which the methionine repressor is deleted, intracellular S-adenosylmethionine synthetase activity is attenuated, and intracellular homoserine transsuccinylase activity, cystathionine γ-synthase activity, and aspartokinase-homoserine dehydrogenase II activity are enhanced. AJ13425 was deposited on May 14, 1998 at the National Institute of Bioscience and Human Technology, Agency of Industrial Science and Technology, Ministry of International Trade and Industry (currently National Institute of Advanced Industrial Science and Technology, International Patent Organism Depository, Address: Tsukuba Central 6, 1-1, Higashi 1-Chome, Tsukuba-shi, Ibaraki-ken, 305-8566, Japan), and assigned an accession number of TERM P-16808.

Because cystathionine and homocysteine are intermediates of the L-methionine biosynthesis pathway, it is effective to partially use the aforementioned methods to enhance the ability to produce L-methionine to enhance abilities to produce these substances. As specific methods for enhancing the ability to produce cystathionine, a method of using a methionine-auxotrophic mutant strain (Japanese Patent Application No. 2003-010654) and a method adding cysteine (or raw material for biosynthesis thereof) and/or homoserine (or raw material for biosynthesis thereof) to a fermentation medium (Japanese Patent Laid-open (Kokai) No. 2005-168422) are known. Since homocysteine is produced by using cystathionine as a precursor, the aforementioned methods for enhancing the ability to produce cystathionine are also effective for enhancing the ability to produce homocysteine.

Because L-methionine is a precursor of S-adenosylmethionine, for enhancing the ability to produce S-adenosylmethionine, it is effective to partially use the aforementioned methods for enhancing the ability to produce L-methionine. For example, the ability to produce S-adenosylmethionine can be imparted or enhanced by enhancing the methionine adenosyltransferase (European Patent Laid-open Nos. 0647712 and 1457569) or by enhancing the secretion factor MdfA (U.S. Pat. No. 7,410,789).

The bacterium can be obtained by modifying such a bacterium belonging to the family Enterobacteriaceae and having L-cysteine-producing ability as mentioned above so that the activity of the protein encoded by the yciW gene (henceforth also referred to as "YciW") is reduced. Alternatively, after a bacterium is modified so that the activity of the YciW protein is reduced, L-cysteine-producing ability can be imparted.

The term yciW gene is synonymous with ECK1282 and JW5200.

The expression "the activity of the protein encoded by the yciW gene is reduced" can mean that the activity of the YciW protein encoded by the yciW gene is decreased compared with that of a non-modified strain such as a wild-type strain or a parent strain, and includes when the activity has completely disappeared.

Such modification that the activity of the YciW protein is reduced can be attained by, for example, reducing expression of the yciW gene. Specifically, for example, the intracellular activity of the protein can be reduced by deleting a part or all of the coding region of the yciW gene on a chromosome. The activity of the YciW protein can also be decreased by reducing expression of the yciW gene by modifying an expression control sequence such as the promoter and the Shine-Dalgarno (SD) sequence of the yciW gene, and so forth. Furthermore, the expression amount of the gene can also be reduced by modifying a non-translation region other than the expression control sequence. Furthermore, the entire gene including the sequences on both sides of the gene on a chromosome can be deleted. Furthermore, it can also be attained by introduction of an amino acid substitution (missense mutation), a stop codon (nonsense mutation), or a frame shift mutation which adds or deletes one or two nucleotides, into the coding region of the yciW gene on a chromosome (Journal of Biological Chemistry, 272:8611-8617 (1997); Proceedings of the National Academy of Sciences, USA, 95 5511-5515 (1998); Journal of Biological Chemistry, 266, 20833-20839 (1991)). Furthermore, expression of the gene can also be reduced by manipulating a factor involved in expression control (low molecules involved in transcription or translation control (inducer, inhibitor, etc.), proteins (transcription factor etc.), nucleic acids (sRNA etc.), and so forth).

Furthermore, the modification can be a modification caused by conventional mutagenesis based on X-ray or ultraviolet irradiation or use of a mutagen such as N-methyl-N'-nitro-N-nitrosoguanidine, so long as it is a modification that the activity of the YciW protein is decreased.

A modification of an expression control sequence can be performed for one or more nucleotides, two or more nucleotides, or three or more nucleotides. When a coding region is deleted, the region to be deleted can be any of an N-terminus region, an internal region, or a C-terminus region, or even can be the entire coding region, so long as the function of the YciW protein is decreased or deleted. Deletion of a longer region can usually more surely inactivate a gene. Furthermore, the reading frames upstream and downstream of the region to be deleted do not have to be the same.

Furthermore, a modification for reducing the activity of the YciW protein can also be attained by inserting another sequence into the coding region of the yciW gene. When another sequence is inserted into the coding region of the yciW gene, such a sequence can be inserted into any region of the gene, and insertion of a longer sequence will more surely inactivate the gene. The reading frames upstream and downstream of the insertion site do not have to be the same. The other sequence is not particularly limited so long as the inserted sequence decreases or deletes the function of the YciW protein, and examples include a transposon carrying an antibiotic resistance gene or a gene useful for L-cysteine production, and so forth.

The yciW gene on the chromosome can be modified as described above by, for example, preparing a deletion-type gene in which a partial sequence of the gene is deleted so that the deletion-type gene does not produce normally functioning YciW protein, and transforming a bacterium with a DNA containing the deletion-type gene to cause homologous recombination between the deletion-type gene and the gene on the chromosome, and thereby substituting the deletion-type gene for the gene on the chromosome. The YciW protein encoded by the deletion-type gene has a conformation different from that of the wild-type protein, if it is even produced, and thus the function is reduced or deleted. Such gene disruption based on gene substitution utilizing homologous recombination has been already established, and methods include "Red-driven integration" (Datsenko, K. A, and Wanner, B. L., Proc. Natl. Acad. Sci. USA, 97:6640-6645 (2000)), a method using a linear DNA such as a method utilizing the Red driven integration in combination with an excision system derived from λ phage (Cho, E. H., Gumport, R. I., Gardner, J. F., J. Bacteriol., 184:5200-5203 (2002)) (refer to WO2005/010175), a method using a plasmid containing a temperature sensitive replication origin, a method using a plasmid capable of conjugative transfer, a method utilizing a suicide vector not having replication origin in a host (U.S. Pat. No. 6,303,383, Japanese Patent Laid-open No. 05-007491), and so forth.

Decrease of the transcription amount of the yciW gene can be confirmed by comparing the amount of mRNA transcribed from the gene with that observed in a wild-type strain or non-modified strain. Examples of the method for evaluating mRNA amount include Northern hybridization, RT-PCR (Molecular Cloning, Cold Spring Harbor Laboratory Press, Cold Spring Harbor, USA, 2001), and so forth.

Decrease of the amount of the YciW protein can be confirmed by Western blotting using antibodies (Molecular cloning, Cold spring Harbor Laboratory Press, Cold spring Harbor, USA, 2001).

plate and synthetic oligonucleotides prepared on the basis of the nucleotide sequence of SEQ ID NO: 1.

Examples of the yciW gene homologues of bacteria other than *Escherichia coli* can include the yciW genes of the following bacteria. In Table 1, Identity (%) indicates the identity between the YciW protein of the *Escherichia coli* K12 strain and the homologue of each bacterium determined by BLAST. The accession numbers are the accession numbers of the NCBI database.

TABLE 1

| Strain | Annotation | Identity (%) | Accession Number |
| --- | --- | --- | --- |
| *Shigella dysenteriae* 1012 | conserved hypothetical protein | 96 | ZP_03066078 |
| *Shigella flexneri* 2a str. 2457T | putative oxidoreductase | 96 | NP_836979 |
| *Shigella boydii* CDC 3083-94 | hypothetical protein | 94 | YP_001880125 |
| *Shigella boydii* Sb227 | putative oxidoreductase | 94 | YP_408203 |
| *Escherichia albertii* TW07627 | putative oxidoreductase | 77 | ZP_02903357 |
| *Citrobacter koseri* ATCC BAA-895 | hypothetical protein | 60 | YP_001452946 |
| *Citrobacter youngae* ATCC 29220 | hypothetical protein | 58 | ZP_03836971 |
| *Citrobacter* sp. 30_2 | conserved hypothetical protein | 57 | ZP_04562177 |
| *Escherichia fergusonii* ATCC 35469 | putative amidase or amidotransferase | 54 | YP_002382809 |
| *Salmonella enterica* subsp. *Enterica* serovar Tennessee str. CDC07-0191 | hypothetical protein | 53 | ZP_04655747 |
| *Klebsiella pneumoniae* | hypothetical protein | 54 | YP_002238976 |
| *Cronobacter turicensis* | Uncharacterized protein | 48 | YP_003210691 |
| *Enterobacter sakazakii* ATCC BAA-894 | hypothetical protein | 47 | YP_001437680 |
| *Enterobacter* sp. 638 | putative oxidoreductase | 46 | YP_001176905 |
| *Salmonella typhimurium* LT2 | putative cytoplasmic protein | 50 | NP_460660 |
| *Pantoea* sp. At-9b | conserved hypothetical protein | 41 | ZP_05729283 |
| *Erwinia pyrifoliae* Ep1/96 | hypothetical protein | 39 | YP_002648706 |
| *Erwinia tasmaniensis* Et1/99 | Conserved hypothetical protein | 40 | YP_001907570 |
| *Yersinia intermedia* ATCC 29909 | hypothetical protein | 38 | ZP_04635903 |
| *Yersinia enterocolitica* subsp. *Enterocolitica* 8081 | hypothetical protein | 36 | YP_001006371 |
| *Serratia proteamaculans* 568 | uncharacterized peroxidase-related enzyme | 37 | YP_001478863 |
| *Yersinia pseudotuberculosis* YPIII | hypothetical protein | 34 | YP_001720631 |
| *Acidovorax avenae* subsp. *citrulli* AAC00-1 | uncharacterized peroxidase-related enzyme | 28 | YP_972817 |

The yciW gene of the *Escherichia coli* K12 strain corresponds to a complementary sequence of the sequence at positions 1347004 to 1348131 in the genome sequence registered at the NCBI database as GenBank accession NC_000913 (VERSION NC_000913.2 GI:49175990). Also, the YciW protein is registered as GenBank accession NP_415803 (version NP_415803.2 GI: 90111242, locus_tag="b1287"). The nucleotide sequence containing the yciW gene, and 300 bp of upstream and downstream regions thereof, and the amino acid sequence encoded by this gene are shown as SEQ ID NOS: 1 and 2, respectively.

Since the nucleotide sequence of the yciW gene can differ depending on the genus, species, or strain to which the bacterium belongs, the yciW gene to be modified can be a variant of the nucleotide sequence of the positions 301 to 1428 in the nucleotide sequence of SEQ ID NO: 1. A variant of the yciW gene can be searched for by using BLAST (blast (dot) genome (dot) jp/) or the like with referring to the nucleotide sequence of SEQ ID NO: 1. Furthermore, the variant of the yciW gene can include homologues of the gene, such as genes that can be amplified by PCR using, for example, a chromosome of such a microorganism as bacteria belonging to the family Enterobacteriaceae and coryneform bacteria as a template and synthetic oligonucleotides prepared on the basis of the nucleotide sequence of SEQ ID NO: 1.

The yciW gene can also be a gene coding for a protein having the amino acid sequence of the YciW protein as mentioned above, but which can include substitution, deletion, insertion, addition, or the like of one or several amino acid residues at one or several positions, so long as it codes for a protein, reduction of which activity in the bacterium results in improvement of L-cysteine-producing ability. Although the number meant by the term "one or several" can differ depending on positions of amino acid residues in the three-dimensional structure of the protein or types of amino acid residues, specifically, it can be 1 to 20, 1 to 10, or preferably 1 to 5. The above substitution, deletion, insertion, or addition of one or several amino acid residues can be a conservative mutation that maintains normal function of the protein. The conservative mutation is typically a conservative substitution. The conservative substitution is a mutation wherein substitution takes place mutually among Phe, Trp and Tyr, if the substitution site is an aromatic amino acid; among Leu, Ile and Val, if it is a hydrophobic amino acid; between Gln and Asn, if it is a polar amino acid; among Lys, Arg and His, if it is a basic amino acid; between Asp and Glu, if it is an acidic amino acid; and between Ser and Thr, if it is an amino acid having hydroxyl group. Specific examples of conservative substitutions include: substitution of Ser or Thr for Ala; substitution of Gln, His or Lys for Arg; substitution of Glu, Gln, Lys, His or Asp for Asn; substitution of Asn, Glu or Gln for Asp;

substitution of Ser or Ala for Cys; substitution of Asn, Glu, Lys, His, Asp or Arg for Gln; substitution of Gly, Asn, Gln, Lys or Asp for Glu; substitution of Pro for Gly; substitution of Asn, Lys, Gln, Arg or Tyr for His; substitution of Leu, Met, Val or Phe for Ile; substitution of Ile, Met, Val or Phe for Leu; substitution of Asn, Glu, Gln, His or Arg for Lys; substitution of Ile, Leu, Val or Phe for Met; substitution of Trp, Tyr, Met, Ile or Leu for Phe; substitution of Thr or Ala for Ser; substitution of Ser or Ala for Thr; substitution of Phe or Tyr for Trp; substitution of His, Phe or Trp for Tyr; and substitution of Met, Ile or Leu for Val. The above-mentioned amino acid substitution, deletion, insertion, addition, inversion etc. can be a result of a naturally-occurring mutation (mutant or variant) due to an individual difference, a difference of species, or the like of a bacterium from which the gene is derived.

Furthermore, the gene having such a conservative mutation as mentioned above can be a gene coding for a protein showing a homology of 80% or more, 90% or more, 95% or more, 97% or more, or even 99% or more, to the total amino acid sequence of the encoded protein, and having a function equivalent to that of the wild-type YciW protein. "Homology" can mean "identity".

Furthermore, the yciW gene can be a DNA that is able to hybridize with a probe that can be prepared from a known gene sequence, such as the aforementioned gene sequence or a complementary sequence thereof, under stringent conditions, and codes for a protein having a function equivalent to that of the YciW protein. The "stringent conditions" can refer to conditions under which a so-called specific hybrid is formed, and a non-specific hybrid is not formed. Examples of the stringent conditions include those under which highly homologous DNAs hybridize to each other, for example, DNAs not less than 80% homologous, not less than 90% homologous, not less than 95% homologous, not less than 97% homologous, or not less than 99% homologous, hybridize to each other, and DNAs less homologous than the above do not hybridize to each other, or conditions of washing of typical Southern hybridization, i.e., conditions of washing once, preferably 2 or 3 times, at a salt concentration and temperature corresponding to 1×SSC, 0.1% SDS at 60° C., 0.1×SSC, 0.1% SDS at 60° C., or 0.1×SSC, 0.1% SDS at 68° C.

The probe can be a part of a sequence complementary to the gene. Such a probe can be prepared by PCR using oligonucleotides prepared on the basis of a known gene sequence as primers and a DNA fragment containing the nucleotide sequence as a template. For example, when a DNA fragment having a length of about 300 bp is used as the probe, the washing conditions of the hybridization can be, for example, 50° C., 2×SSC and 0.1% SDS.

The aforementioned explanation of the variants of genes and proteins are also similarly applied to enzymes such as serine acetyltransferase and 3-phosphoglycerate dehydrogenase and the YdeD protein, as well as the genes coding for them.

<2> Method for Producing L-Cysteine, L-Cystine, Derivative Thereof, or Mixture Thereof By culturing the bacterium obtained as described above in a medium and collecting L-cysteine, L-cystine, a derivative thereof, or a mixture thereof from the medium, these compounds can be produced. Examples of the derivative of L-cysteine include S-sulfocysteine, thiazolidine derivatives, hemithioketals corresponding to the thiazolidine derivatives, and so forth as mentioned above. γ-glutamylcysteine, glutathione, cystathionine, homocysteine, methionine, S-adenosylmethionine, and so forth, which are biosynthesized from L-cysteine as a starting material, can also be produced in a similar manner.

As the medium to be used, ordinary media containing a carbon source, nitrogen source, sulfur source, inorganic ions, and other organic components as required can be mentioned.

As the carbon source, saccharides such as glucose, fructose, sucrose, molasses, and starch hydrolysate, and organic acids such as fumaric acid, citric acid, and succinic acid can be used.

As the nitrogen source, inorganic ammonium salts such as ammonium sulfate, ammonium chloride, and ammonium phosphate, organic nitrogen such as soybean hydrolysate, ammonia gas, aqueous ammonia, and so forth can be used.

As the sulfur source, inorganic sulfur compounds such as sulfates, sulfites, sulfides, hyposulfites, and thiosulfates can be mentioned.

As organic trace amount nutrients, required substances such as vitamin $B_1$, yeast extract, and so forth in appropriate amounts can be added. Other than these, potassium phosphate, magnesium sulfate, iron ions, manganese ions, and so forth are added in small amounts, as required.

The culture can be performed under aerobic conditions for 30 to 90 hours. The culture temperature can be controlled to be at 25° C. to 37° C., and pH can be controlled to be 5 to 8 during the culture. To adjust the pH, inorganic or organic acidic or alkaline substances, ammonia gas, and so forth can be used. Collection of L-cysteine from the culture broth can be attained by a combination of ordinary ion exchange resin method, precipitation, and other known methods.

L-cysteine obtained as described above can be used for production of L-cysteine derivatives. The L-cysteine derivatives include methylcysteine, ethylcysteine, carbocisteine, sulfocysteine, acetylcysteine, and so forth.

Furthermore, when a thiazolidine derivative of L-cysteine is accumulated in the medium, L-cysteine can be produced by collecting the thiazolidine derivative from the medium and breaking the reaction equilibrium between the thiazolidine derivative and L-cysteine so that L-cysteine is excessively produced.

Furthermore, when S-sulfocysteine is accumulated in the medium, it can be converted into L-cysteine by reduction using a reducing agent such as dithiothreitol.

Example

Hereafter, the present invention will be explained more specifically with reference to the following non-limiting example.

(1) Construction of yciW Gene-Deficient Strain

Deletion of the yciW gene was performed by the method called "Red-driven integration", first developed by Datsenko and Wanner (Proc. Natl. Acad. Sci. USA, 2000, vol. 97, No. 12, pp. 6640-6645). According to the "Red-driven integration" method, by using a PCR product obtained with synthetic oligonucleotides designed so that a part of a target gene is present on the 5' end, and a part of an antibiotic resistance gene is present on the 3' end, respectively, as primers, a gene-disrupted strain can be constructed in one step. A method for deleting a gene of *E. coli* using this "Red-driven integration" and the excision system derived from λ phage is described in detail in Japanese Patent Laid-open (Kokai) No. 2005-058227 (U.S. Patent Published Application No. 2006154344), WO2007/119880A1, and so forth. A yciW gene-deficient strain was obtained by the same methods.

A DNA fragment which includes homologous sequences from both ends of the yciW gene, and an antibiotic resistance gene (kanamycin resistance gene (Km$^r$)) between them, was obtained by PCR. The specific experimental methods and materials are the same as described in Japanese Patent Laid-open (Kokai) No. 2005-058227 (U.S. Patent Published Application No. 2006154344) except that DyciWec-FW (SEQ ID NO: 3, ATGGAACAACGCCACATCACCG- GCAAAAGCCACTGGTATCATGAAACGCATG AAGC- CTGCTTTTTTATACTAAGTTGGCA), and DyciWec-RV (SEQ ID NO: 4, CCCATTGGTTAATTTCATTTTCGCCCT- TGCGCATAAGGGTGCTGATTTTTCGCT CAAGTTAG- TATAAAAAAGCTGAACGA) were used as primers, and a DNA fragment containing the λattL-Km$^r$-λattR sequence derived from pMW118-(λttL-Km$^r$-λttR) (WO2006/093322A2) was used as a template.

By this method, a yciW gene-deficient strain, MG1655ΔyciW::Kmr, was obtained from the *E. coli* MG1655 strain (ATCC 47076).

In addition, the Km$^r$ gene incorporated into the yciW gene-disrupted strain can be removed by using the excision system derived from λ phage.

(2) Construction of L-Cysteine-Producing Bacterium pACYC-DES, a single plasmid into which a mutant cysE coding for a mutant serine acetyltransferase which is not subject to feedback inhibition by L-cysteine (U.S. Patent Published Application No. 20050112731(A1)), the ydeD gene coding for an L-cysteine secretion factor (U.S. Pat. No. 5,972,663), and a mutant serA gene coding for a 3-phosphoglycerate dehydrogenase which is not subject to feedback inhibition by L-serine (U.S. Pat. No. 6,180,373) were integrated, was introduced into the *E. coli* MG1655 strain and the MG1655DyciW::Kmr strains. In the aforementioned mutant serine acetyltransferase, the threonine residue at position 167 was replaced with an alanine residue. Furthermore, in the aforementioned 3-phosphoglycerate dehydrogenase, the tyrosine residue at position 410 was deleted. The construction of pACYC-DES is described in Japanese Patent Laid-open (Kokai) No. 2005-137369 (U.S. Patent Published Application No. 20050124049(A1), European Patent Laid-open No. 1528108(A1)).

(3) L-Cysteine Production Culture

In order to investigate the effect of the deletion of the yciW gene on the production of L-cysteine and L-cysteine related compounds by fermentation, the aforementioned L-cysteine-producing *E. coli* bacteria, MG1655/pACYC-DES and MG1655DyciW::Kmr/pACYC-DES (yciW deficient), were cultured for the production by fermentation, and amounts of L-cysteine and L-cysteine-related compounds that were produced were compared. For the culture, a cysteine production medium having the following composition was used. As sulfur source for L-cysteine production, sulfate (ammonium sulfate) and thiosulfate (sodium thiosulfate) were used. The culture using only the sulfate was performed without adding the component 6 (sodium thiosulfate) mentioned in the following medium composition. Furthermore, the culture using the thiosulfate was performed by using all the following medium components.

[L-Cysteine Production Medium] (Concentrations of the Components are Final Concentrations)

Components 1:

| | |
|---|---|
| $(NH_4)_2SO_4$ | 15 g/L |
| $KH_2PO_4$ | 1.5 g/L |
| $MgSO_4 \cdot 7H_2O$ | 1 g/L |
| Thiamine hydrochloride | 0.1 mg/L |

Components 2:

| | |
|---|---|
| $FeSO_4 \cdot 7H_2O$ | 1.7 mg/L |
| $Na_2MoO_4 \cdot 2H_2O$ | 0.15 mg/L |
| $CoCl_2 \cdot 6H_2O$ | 0.7 mg/L |
| $MnCl \cdot 4H_2O$ | 1.6 mg/L |
| $ZnSO_4 \cdot 7H_2O$ | 0.3 mg/L |
| $CuSO_4 \cdot 5H_2O$ | 0.25 mg/L |

Components 3:

| | |
|---|---|
| Tryptone | 0.6 g/L |
| Yeast extract | 0.3 g/L |
| NaCl | 0.6 g/L |

Component 4:

| | |
|---|---|
| Calcium carbonate | 20 g/L |

Component 5:

| | |
|---|---|
| L-Histidine hydrochloride monohydrate | 135 mg/L |

Component 6:

| | |
|---|---|
| Sodium thiosulfate | 4 g/L |

Component 7:

| | |
|---|---|
| Pyridoxine hydrochloride | 2 mg/L |

Component 8:

| | |
|---|---|
| Glucose | 40 g/L |

For these components, the following stock solutions were prepared: 10-fold concentration (Components 1), 1000-fold concentration (Components 2), 100/6-fold concentration (Components 3), 100-fold concentration (Component 5), 350/4-fold concentration (Component 6), 1000-fold concentration (Component 7), and 10-fold concentration (Component 8), they were mixed at the time of use, and the defined volume was obtained with sterilized water to attain the final concentrations. Sterilization was performed by autoclaving at 110° C. for 30 minutes (Components 1, 2, 3, 5, and 8), dry heat sterilization at 180° C. for 5 hours or longer (Component 4), or filter sterilization (Components 6 and 7).

The L-cysteine production culture was performed as follows. Each production strain was spread on the LB agar medium to perform pre-culture overnight at 37° C., and then cells corresponding to about 7 cm on the plate were scraped with an inoculation loop of 10-μl size (NUNC Blue Loop) three times (three loops), and inoculated into 2 ml of the L-cysteine production medium contained in a large test tube (internal diameter: 23 mm, length: 20 cm) so as to make cell amounts for both the strains at the time of the start of the culture substantially the same. Culture was performed at 32° C. with shaking, and terminated after 25 hours. L-cysteine (including L-cysteine-related compounds) produced in the medium was quantified by the method described by Gaitonde, M. K. (Biochem. J., 104(2):627-33, August 1967). The experiment was performed quadruplicate for each strain, and the produced L-cysteine amounts (averages) and standard deviations, and L-cysteine yields for the consumed glucose are shown in Table 2. In Table 2, the wild-type strain means the MG1655/pACYC-DES strain, and the yciW deletion strain means the MG1655DyciW::Kmr/pACYC-DES strain. These results show that deletion of the yciW gene resulted in increasing accumulation of L-cysteine for both sulfur sources.

TABLE 2

| Sulfur Source | Strain | L-cysteine (g/L) | Yield for Consumed Sugar (%) |
|---|---|---|---|
| sulfate | wild-type strain | 0.5 ± 0.02 | 1.4 ± 0.07 |
|  | yciW deletion strain | 1.7 ± 0.04 | 5.0 ± 0.21 |
| sulfate and | wild-type strain | 1.4 ± 0.05 | 3.9 ± 0.12 |
| thiosulfate | yciW deletion strain | 1.8 ± 0.37 | 5.7 ± 1.29 |

While the invention has been described in detail with reference to preferred embodiments thereof, it will be apparent to one skilled in the art that various changes can be made, and equivalents employed, without departing from the scope of the invention. Each of the aforementioned documents is incorporated by reference herein in its entirety.

The invention claimed is:

1. A bacterium belonging to the family Enterobacteriaceae, which is able to produce L-cysteine, and is modified to have reduced activity of a protein encoded by the yciW gene, as compared to a non-modified bacterium, by reducing expression of the yciW gene or by disrupting the yciW gene.

2. The bacterium according to claim 1, wherein the protein is selected from the group consisting of:
   (A) a protein comprising the amino acid sequence shown in SEQ ID NO: 2,
   (B) a protein comprising the amino acid sequence shown in SEQ ID NO: 2, but which includes substitutions, deletions, insertions, or additions of 1 to 10 amino acid residues,
   wherein said reduced activity results in an improved ability to produce L-cysteine.

3. The bacterium according to claim 1, wherein the yciW gene is a DNA selected from the group consisting of:
   (a) a DNA comprising the nucleotide sequence of the positions 301 to 1428 in the nucleotide sequence of SEQ ID NO: 1,
   (b) a DNA hybridizable with a complementary sequence of the nucleotide sequence of the positions 301 to 1428 in the nucleotide sequence of SEQ ID NO: 1, or a probe that can be prepared from the nucleotide sequence, under stringent conditions comprising washing at 0.1×SSC, 0.1% SDS, 60° C., and which encodes a protein,
   wherein said reduced activity results in an improved ability to produce L-cysteine.

4. The bacterium according to claim 1, which is modified to further comprise at least one of the following characteristics:
   i) serine acetyltransferase activity is increased as compared with a non-modified bacterium,
   ii) expression of the ydeD gene is increased as compared with a non-modified bacterium, and
   iii) 3-phosphoglycerate dehydrogenase activity is increased as compared with a non-modified bacterium.

5. The bacterium according to claim 1, which is an *Escherichia* bacterium.

6. The bacterium according to claim 5, which is *Escherichia coli*.

7. A method for producing L-cysteine, L-cystine, a derivative thereof, or a mixture thereof, which comprises culturing the bacterium according to claim 1 in a medium and collecting L-cysteine, L-cystine, a derivative thereof, or a mixture thereof from the medium.

8. The method according claim 7, wherein the derivative of L-cysteine is a thiazolidine derivative.

* * * * *

SEQUENCE LISTING

```
<160> NUMBER OF SEQ ID NOS: 4

<210> SEQ ID NO 1
<211> LENGTH: 1728
<212> TYPE: DNA
<213> ORGANISM: Escherichia coli
<220> FEATURE:
<221> NAME/KEY: CDS
<222> LOCATION: (301)..(1428)

<400> SEQUENCE: 1
agccgttacc ccgattcgcc gtaccgttac tattgaagat gtgggtaact ctgcggcatt     60
cctgtgctcc gatctctctg ccggtatctc cggtgaagtg gtccacgttg acggcggttt    120
cagcattgct gcaatgaacg aactcgaact gaaataatcg ttctgttggt aaagatgggc    180
ggcgttctgc cgcccgttat ctctgttata cctttctgat atttgttatc gccgatccgt    240
ctttctcccc ttcccgcctt gcgtcaggat aacgatttcc tttacgacca aggagcgccc    300 atg gaa caa cgc cac atc acc ggc aaa agc cac tgg tat cat gaa acg     348
Met Glu Gln Arg His Ile Thr Gly Lys Ser His Trp Tyr His Glu Thr
1               5                   10                  15 caa tcc agt act acg gag tat gac gtt ctg cct ctg gtc ccg gaa gcc     396
Gln Ser Ser Thr Thr Glu Tyr Asp Val Leu Pro Leu Val Pro Glu Ala
            20                  25                  30 gca aag gtc agc gat ccc ttt cta ctc gac gtg atc ctt gaa aaa gaa     444
Ala Lys Val Ser Asp Pro Phe Leu Leu Asp Val Ile Leu Glu Lys Glu
        35                  40                  45 acg ctg gcc ccc ttc ctt tca tgg ctg gac cct gcg cgt gtt ctt gca     492
Thr Leu Ala Pro Phe Leu Ser Trp Leu Asp Pro Ala Arg Val Leu Ala
    50                  55                  60 gtg gat ttg ttc cct gac cag ctt acc gtg acc cgt tca cag acc ttc     540
Val Asp Leu Phe Pro Asp Gln Leu Thr Val Thr Arg Ser Gln Thr Phe
65                  70                  75                  80 acc gct tat gaa cgc ttg tcg acg gcc ctg acg gtt gct cag gtt tgc     588
Thr Ala Tyr Glu Arg Leu Ser Thr Ala Leu Thr Val Ala Gln Val Cys
                85                  90                  95 ggc gtc cag cgg tta tgt aac tac tat tcg gcg cga ctt acg ccg ctc     636
Gly Val Gln Arg Leu Cys Asn Tyr Tyr Ser Ala Arg Leu Thr Pro Leu
            100                 105                 110 ccc ggg cct gat tcc acc agg gaa agt aat cat cgg ttg gca caa atc     684
Pro Gly Pro Asp Ser Thr Arg Glu Ser Asn His Arg Leu Ala Gln Ile
        115                 120                 125 acg caa tat gcc cgc caa ctg gct agc tcg cct tct att atc gac aac     732
Thr Gln Tyr Ala Arg Gln Leu Ala Ser Ser Pro Ser Ile Ile Asp Asn
```

```
                130                 135                 140
cga tcg cgc cag cat ctg aat gac gtc ggt ctt act gcc tgg gac tgt     780
Arg Ser Arg Gln His Leu Asn Asp Val Gly Leu Thr Ala Trp Asp Cys
145                 150                 155                 160 gtg atc att agc caa atc att ggt ttt att ggc ttt cag gcg cgg aca     828
Val Ile Ile Ser Gln Ile Ile Gly Phe Ile Gly Phe Gln Ala Arg Thr
                165                 170                 175 att gcg aca ttt cag gct tat ctc ggg cat ccg gta cgc tgg tta ccc     876
Ile Ala Thr Phe Gln Ala Tyr Leu Gly His Pro Val Arg Trp Leu Pro
            180                 185                 190 ggg ctg gag ata caa aac tac gcc gac gcg tca ctg ttt gct gat gaa     924
Gly Leu Glu Ile Gln Asn Tyr Ala Asp Ala Ser Leu Phe Ala Asp Glu
        195                 200                 205 tca tta cgc tgg cga agc agc tat gag gtg gaa aaa cta cct gaa gag     972
Ser Leu Arg Trp Arg Ser Ser Tyr Glu Val Glu Lys Leu Pro Glu Glu
    210                 215                 220 cac aca aaa agt tca act gca gaa ctt tgc caa ctg gcc gaa ata ctc    1020
His Thr Lys Ser Ser Thr Ala Glu Leu Cys Gln Leu Ala Glu Ile Leu
225                 230                 235                 240 tct ctc cac cct att tca ctt tcc ctt ctc gaa aag ttg tta aac agc    1068
Ser Leu His Pro Ile Ser Leu Ser Leu Leu Glu Lys Leu Leu Asn Ser
                245                 250                 255 aca cgg ggc aat aca cag ccg gat aat cag ctt gcg gcg ttg tta tgc    1116
Thr Arg Gly Asn Thr Gln Pro Asp Asn Gln Leu Ala Ala Leu Leu Cys
            260                 265                 270 gcg cgt ata aat ggc agt cct gct tgt ttt gcc acc tgt atg gat tca    1164
Ala Arg Ile Asn Gly Ser Pro Ala Cys Phe Ala Thr Cys Met Asp Ser
        275                 280                 285 tca aat gaa tat aaa aaa atc agc acc ctt atg cgc aag ggc gaa aat    1212
Ser Asn Glu Tyr Lys Lys Ile Ser Thr Leu Met Arg Lys Gly Glu Asn
    290                 295                 300 gaa att aac caa tgg gct gac cgt cat tct gtt gag cgc gct acc gtt    1260
Glu Ile Asn Gln Trp Ala Asp Arg His Ser Val Glu Arg Ala Thr Val
305                 310                 315                 320 cag gcg ata caa tgg ctg acc cga gca ccc gat cgc ttt agc gcc gcc    1308
Gln Ala Ile Gln Trp Leu Thr Arg Ala Pro Asp Arg Phe Ser Ala Ala
                325                 330                 335 cag ttc agc cct tta ctc gaa cac gaa aaa tca tca acg cag att att    1356
Gln Phe Ser Pro Leu Leu Glu His Glu Lys Ser Ser Thr Gln Ile Ile
            340                 345                 350 aat ctg ctg gta tgg agc ggg ctg tgt ggc tgg ata aat cgc tta aaa    1404
Asn Leu Leu Val Trp Ser Gly Leu Cys Gly Trp Ile Asn Arg Leu Lys
        355                 360                 365 atc gcg ttg ggt gag aca tat taa ccttgccgcg tcagacagat tcgcgtaaaa   1458
Ile Ala Leu Gly Glu Thr Tyr
    370                 375 ctgtcagccg ctctaatggc caccaaaata gacaattatg tttcaggaca acccgctgct  1518
agcgcagctt aaacagcaac tgcattccca gacgccacgc gctgaagggg tggtaaaagc  1578
cacagaaaaa ggctttggct tcctggaagt cgacgcgcaa aaagttatt tcattccgcc   1638 gccgcagatg aaaaaagtca tgcatggcga ccgaattatc gcggtgatcc acagtgaaaa  1698
agaacgtgaa tccgcagagc cagaagaact                                   1728

<210> SEQ ID NO 2
<211> LENGTH: 375
<212> TYPE: PRT
<213> ORGANISM: Escherichia coli

<400> SEQUENCE: 2
```

```
Met Glu Gln Arg His Ile Thr Gly Lys Ser His Trp Tyr His Glu Thr
1               5                   10                  15

Gln Ser Ser Thr Thr Glu Tyr Asp Val Leu Pro Leu Val Pro Glu Ala
            20                  25                  30

Ala Lys Val Ser Asp Pro Phe Leu Leu Asp Val Ile Leu Glu Lys Glu
        35                  40                  45

Thr Leu Ala Pro Phe Leu Ser Trp Leu Asp Pro Ala Arg Val Leu Ala
50                  55                  60

Val Asp Leu Phe Pro Asp Gln Leu Thr Val Thr Arg Ser Gln Thr Phe
65                  70                  75                  80

Thr Ala Tyr Glu Arg Leu Ser Thr Ala Leu Thr Val Ala Gln Val Cys
            85                  90                  95

Gly Val Gln Arg Leu Cys Asn Tyr Tyr Ser Ala Arg Leu Thr Pro Leu
        100                 105                 110

Pro Gly Pro Asp Ser Thr Arg Glu Ser Asn His Arg Leu Ala Gln Ile
            115                 120                 125

Thr Gln Tyr Ala Arg Gln Leu Ala Ser Ser Pro Ser Ile Ile Asp Asn
130                 135                 140

Arg Ser Arg Gln His Leu Asn Asp Val Gly Leu Thr Ala Trp Asp Cys
145                 150                 155                 160

Val Ile Ile Ser Gln Ile Ile Gly Phe Ile Gly Phe Gln Ala Arg Thr
            165                 170                 175

Ile Ala Thr Phe Gln Ala Tyr Leu Gly His Pro Val Arg Trp Leu Pro
        180                 185                 190

Gly Leu Glu Ile Gln Asn Tyr Ala Asp Ala Ser Leu Phe Ala Asp Glu
            195                 200                 205

Ser Leu Arg Trp Arg Ser Ser Tyr Glu Val Lys Leu Pro Glu Glu
210                 215                 220

His Thr Lys Ser Ser Thr Ala Glu Leu Cys Gln Leu Ala Glu Ile Leu
225                 230                 235                 240

Ser Leu His Pro Ile Ser Leu Ser Leu Leu Glu Lys Leu Leu Asn Ser
            245                 250                 255

Thr Arg Gly Asn Thr Gln Pro Asp Asn Gln Leu Ala Ala Leu Leu Cys
        260                 265                 270

Ala Arg Ile Asn Gly Ser Pro Ala Cys Phe Ala Thr Cys Met Asp Ser
        275                 280                 285

Ser Asn Glu Tyr Lys Lys Ile Ser Thr Leu Met Arg Lys Gly Glu Asn
        290                 295                 300

Glu Ile Asn Gln Trp Ala Asp Arg His Ser Val Glu Arg Ala Thr Val
305                 310                 315                 320

Gln Ala Ile Gln Trp Leu Thr Arg Ala Pro Asp Arg Phe Ser Ala Ala
                325                 330                 335

Gln Phe Ser Pro Leu Leu Glu His Glu Lys Ser Ser Thr Gln Ile Ile
            340                 345                 350

Asn Leu Leu Val Trp Ser Gly Leu Cys Gly Trp Ile Asn Arg Leu Lys
            355                 360                 365

Ile Ala Leu Gly Glu Thr Tyr
370                 375

<210> SEQ ID NO 3
<211> LENGTH: 80
<212> TYPE: DNA
<213> ORGANISM: Artificial Sequence
<220> FEATURE:
<223> OTHER INFORMATION: primer DyciWec-FW
```

```
<400> SEQUENCE: 3
atggaacaac gccacatcac cggcaaaagc cactggtatc atgaaacgca tgaagcctgc    60 tttttatac taagttggca                                                 80

<210> SEQ ID NO 4
<211> LENGTH: 80
<212> TYPE: DNA
<213> ORGANISM: Artificial Sequence
<220> FEATURE:
<223> OTHER INFORMATION: primer DyciWec-RV

<400> SEQUENCE: 4
cccattggtt aatttcattt tcgcccttgc gcataagggt gctgatttt cgctcaagtt     60 agtataaaaa agctgaacga                                                80
```